US00PP15031P2

(12) United States Plant Patent
White

(10) Patent No.: US PP15,031 P2
(45) Date of Patent: Jul. 27, 2004

(54) CLEMATIS PLANT NAMED 'SNOW VALLEY'

(50) Latin Name: *Clematis×cartmanii*
Varietal Denomination: Snow Valley

(76) Inventor: Anthony Robin White, Kilmeston, Alresford, Hants (GB), S024 ONL ( * ) Notice: Subject to any disclaimer, the term of this patent is extended or adjusted under 35 U.S.C. 154(b) by 131 days.

(21) Appl. No.: 10/241,702

(22) Filed: Sep. 11, 2002

(51) Int. Cl.[7] ..... A01H 5/00
(52) U.S. Cl. ..... Plt./228
(58) Field of Search ..... Plt./228

*Primary Examiner*—Bruce R. Campell
*Assistant Examiner*—Michelle Kizilkaya

(57) ABSTRACT

A new cultivar of Clematis named 'Snow Valley' that is characterized by a compact habit, fernlike foliage and a profuse display of cream-white female flowers in spring. In combination these traits set 'Snow Valley' apart from all other existing varieties of Clematis known to the inventor.

2 Drawing Sheets

Genus: Clematis.
Species: *cartmanii.*
Denomination: Snow Valley.

BACKGROUND OF THE INVENTION

The present invention relates to a new and distinct cultivar of Clematis that is grown for use as a sub-shrub for the landscape. The new cultivar is known botanically as a *Clematis×cartmanii* and will be referred to hereinafter by the cultivar name 'Snow Valley'.

'Snow Valley' resulted from a formal breeding program. The inventor bred 'Snow Valley' in 1994 by induced hybridization between the pollen parent Clematis 'Avalanche' (unpatented) and the seed parent Clematis 'White Cascade' (unpatented). The cross was conducted in a cultivated area of Hampshire, England and 'Snow Valley' was selected based on the criteria of compact habit and female sexuality. 'Snow Valley' is a hybrid and exhibits short internodes and a profusion of cream-white flowers, along with finely dissected green foliage with grey-purple markings.

The closest comparison plant is *Clematis×cartmanii* 'Early Sensation' (unpatented). 'Snow Valley' is distinguishable from the comparison plant by its pronounced compact habit. At maturity 'Snow Valley' is 0.3 meters in height and 0.5 meters in width. 'Snow Valley' differs from the parent plants 'Avalanche' and 'White Cascade' in vigor, internode length, finely dissected leaves, and flower size. 'White Cascade' and 'Avalanche' grow 10–16 cm. in a season. 'Snow Valley' is less vigorous, growing 5–6 cm. in a season. The internode length of 'Snow Valley' is 3–4 cm. This is less than 'White Cascade' and 'Avalanche', which exhibit internodes that are 10–16 cm. in length. The leaves of 'Snow Valley' are finely dissected. 'Snow Valley' exhibits flowers that are 3–4.25 cm. in diameter, whereas 'Avalanche' exhibits flowers that are 7–8 cm. in diameter and 'White Cascade' exhibits flowers that are 5.50–7 cm. in diameter.

The first asexual propagation of 'Snow Valley', was accomplished by the inventor, in 1997 in a cultivated area of Hampshire, England. The method of propagation used was semi-ripe nodal stem cuttings. Since that time, under careful observation, the distinguishing characteristics have been determined stable and uniform and true to type in successive generations.

SUMMARY OF THE INVENTION

The following represent the distinguishing characteristics of the new Clematis cultivar 'Snow Valley'. In combination these traits set 'Snow Valley' apart from all other existing varieties of Clematis known to the inventor. 'Snow Valley' has not been tested under all possible conditions and phenotypic differences may be observed with variations in environmental, climatic, and cultural conditions, however, without any variance in genotype.

1. Clematis 'Snow Valley' is an evergreen sub-shrub.
2. Clematis 'Snow Valley' produces female flowers.
3. Clematis 'Snow Valley' exhibits a compact habit.
4. Clematis 'Snow Valley' exhibits finely dissected green foliage with grey-purple markings.
5. Clematis 'Snow Valley' exhibits short internodes.
6. Clematis 'Snow Valley' produces a profusion of cream-white flowers in spring.
7. Clematis 'Snow Valley' is 0.30 meters in height and 0.50 meters in width at maturity.

BRIEF DESCRIPTION OF THE DRAWINGS

The accompanying color drawings illustrate the overall appearance of the new cultivar 'Snow Valley', showing the colors as true as it is reasonably possible to obtain in colored reproductions of this type. Colors in the drawings may differ from the color values cited in the detailed botanical description, which accurately describe the actual colors of the new variety 'Snow Valley'. The plants in the drawings were grown in an unheated greenhouse in Oregon with minimum night temperatures of minus 6° Centigrade. They were 18-months-old and in one-liter containers at the time. The drawing on sheet 1 illustrates the entire plant in bloom from a side perspective. The drawing on sheet 2 is a close-up view of the flowers. All drawings were made using conventional techniques and although foliage colors may appear different from actual colors due to light reflectance, they are as accurate as possible by conventional photography.

BOTANICAL DESCRIPTION OF THE PLANT

The following is a detailed description of the Clematis cultivar named 'Snow Valley'. Data was collected in Arroyo Grande, Calif. from plants that were grown in an unheated greenhouse with minimum night temperatures of minus 6° Centigrade. The young plants were 9-months-old and in 10 cm. containers and the mature plants were 18-months-old and in one-liter containers at the time. Color determinations are in accordance with The 2001 Royal Horticultural Society Colour Chart except where general color terms of ordinary dictionary significance are used. The growing requirements are similar to the species.

Botanical classification: *Clematis×cartmanii* 'Snow Valley'.
Species: *cartmanii*.
Common name: Vase vine.
Uses: Sub-shrub.
Parentage: 'Snow Valley' is a hybrid resulting from the induced hybridization of the following parent plants: Seed parent: Clematis 'White Cascade'. Pollen parent: Clematis 'Avalanche'.
Type: Perennial.
Vigor: Moderate vigor.
Habit: Compact.
Height (one-liter container): 16 cm. in height.
Width (one-liter container): 42 cm. in width.
Height (10 cm. container): 15 cm. in height.
Width (10 cm. container): 21 cm. in width.
Hardiness: Hardy to minus 10° Centigrade.
Propagation: Semi-ripe nodal stem cuttings.
Root system: Fibrous.
Soil: Any well-drained soil.
Sunlight: Good light intensity.
Plant sexuality: Unisexual.
Time to initiate rooting: 6–8 weeks are needed to produce roots on an initial cutting.
Temperature to initiate rooting: 15° to 21° Centigrade air temperature.
Crop time: 12 to 15 months are needed to produce a finished one-liter container from a rooted cutting.
Seasonal interest: Cream-white flowers in spring.
Stem:
- *Stem diameter.*—4 mm. in diameter.
- *Stem length.*—15 cm. long.
- *Shape.*—Cylindrical.
- *Surface.*—Pubescent and corrugated.
- *Stem color.*—A combination of 147A and N187A.
- *Trunk color.*—N186A.
- *Internode length* (*10 cm. container*).—1.50–3 cm. between nodes.
- *Internode length* (*1-liter container*).—3–4 cm. between nodes.

Foliage:
- *Type.*—Evergreen.
- *Leaf arrangement.*—Opposite.
- *Leaf division.*—Ternate.
- *Leaf shape.*—Trifoliate and finely dissected.
- *Leaf base.*—Aequilateral.
- *Leaf apex.*—Acute at tips of lobes.
- *Leaf venation.*—Pinnate with prominent mid-vein.
- *Vein color* (*abaxial and adaxal surfaces*).—137A.
- *Leaf surface* (*adaxial*).—Glabrous and shiny.
- *Leaf surface* (*abaxial*).—Glabrous and matte.
- *Leaf pubescence.*—Absent.
- *Leaf texture.*—Fine and fern-like.
- *Leaf attachment.*—Petiolate.
- *Petiole dimensions.*—1 cm. in length and 1 mm. in length.
- *Petiole shape.*—Sulcate.
- *Petiole color.*—A combination of N144C and 137A.
- *Petiole surface.*—Pubescent.
- *Leaf margin.*—Lobed with each lobe margin entire.
- *Young leaf dimensions* (*in 10 cm. container*).—0.75 cm. in length and 0.50 cm. in width.
- *Young leaf color on adaxial and abaxial surfaces* (10 cm. container).—A combination of 187A and 137A.
- *Mature leaf dimensions* (*in one-liter container*).—3 cm. in length and 3 cm. in width.
- *Mature leaf color on adaxial and abaxial surfaces* (*in one-liter container*).—A combination of 147A and N187B.
- *Foliar fragrance.*—Absent.

Flower:
- *Inflorescence.*—Panicle.
- *Flower form.*—Solitary.
- *Color of peduncle.*—A combination of 144A and N187A.
- *Peduncle length.*—4 cm. in length.
- *Peduncle diameter.*—2 mm. in diameter.
- *Peduncle form.*—Tortuous.
- *Self-cleaning or persistent.*—Self-cleaning.
- *Sexuality.*—Female.
- *Dimensions of flower.*—2 cm. in height and 3–4.25 cm. in diameter.
- *Flower shape.*—Campanulate to rotate.
- *Aspect.*—Facing outward and downward.
- *Petals.*—Apetalous.
- *Tepals.*—Six to eight in number.
- *Tepal texture.*—Petaloid.
- *Color of tepals* (*adaxial and abaxial surfaces*).—155A.
- *Tepal shape.*—Obdeltoid.
- *Tepal surface* (*adaxial surface*).—Glabrous.
- *Tepal surface* (*abaxial surface*).—Pubescent.
- *Tepal margin.*—Entire with sparse hairs.
- *Tepal apex.*—Rounded.
- *Tepal base.*—Cuneate.
- *Tepal length.*—2 cm. in length.
- *Tepal width.*—1.25 cm. in width.
- *Unfused or fused.*—Tepals are unfused.
- *Subtending bracts.*—Four in number.
- *Dimensions of subtending bracts.*—6 mm. in length and 3 mm. in width.
- *Color of subtending bracts.*—137A.
- *Blooming period.*—March to April.
- *Bud color.*—160C.
- *Bud shape.*—Ovate.
- *Bud dimensions.*—1 cm. in length and 0.75 cm. in width.
- *Quantity of flowers.*—Approximately 10 per inflorescence.
- *Fragrance.*—Absent.

Reproduction organs:
- *Stamens.*—Absent.
- *Rudimentary stamens.*—15 inserted below base of ovary.
- *Anthers.*—Absent.
- *Pollen.*—Absent.
- *Pistil.*—One.
- *Pistil color.*—N144C.
- *Style shape.*—Elongated and plumose.
- *Style color.*—N144C.
- *Stigma.*—Many filaments.
- *Stigma color.*—N144C.
- *Ovary position.*—Superior.
- *Ovary shape.*—Cone shaped.

*Ovary dimensions.*—4 mm. in width and 5 mm. in height.

*Ovary color.*—N144C.

Seed:

*Number of seeds.*—Approximately 22 seeds per fruit.

*Seed color.*—199A.

*Seed dimensions.*—4 mm. in length and 1.50 mm. in width.

*Seed shape.*—Closest to lunate.

*Style shape.*—Plumose.

*Style dimensions.*—2.25 mm. in length and 3 mm. in diameter.

*Style color.*—156D.

I claim:

1. A new and distinct variety of Clematis plant named 'Snow Valley' as described and illustrated.

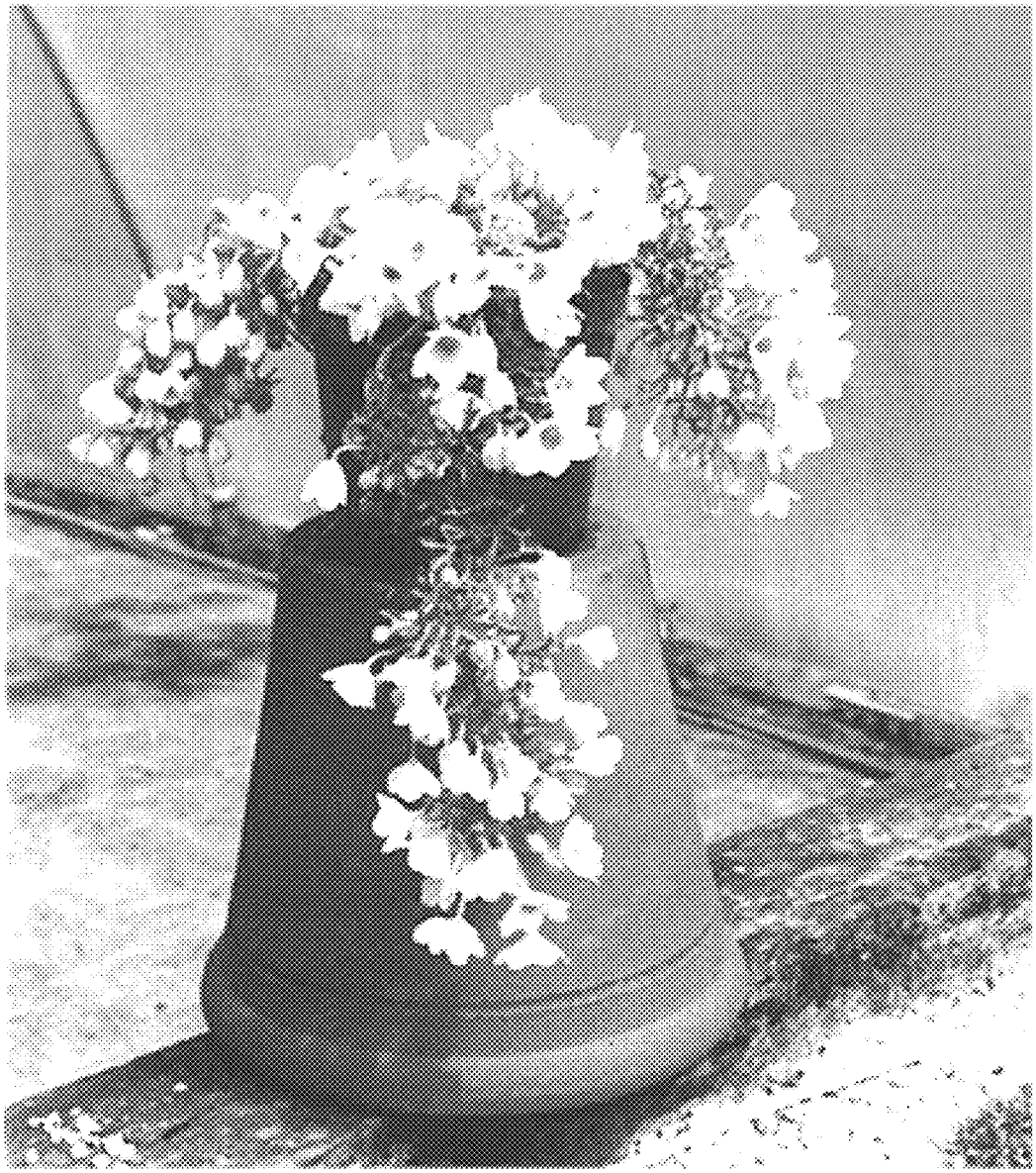

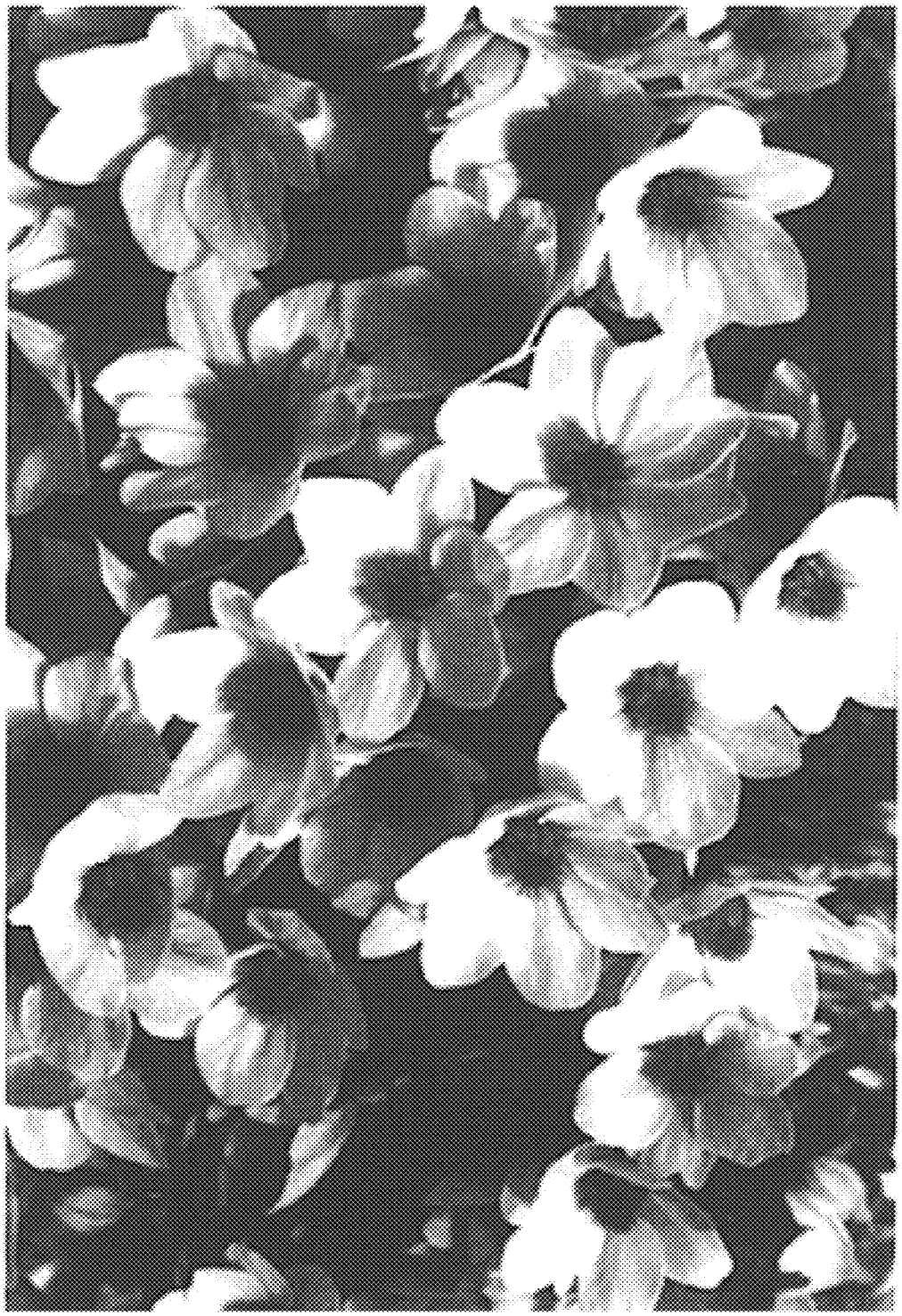

* * * * *